United States Patent
De Bosscher et al.

(10) Patent No.: US 7,053,120 B2
(45) Date of Patent: May 30, 2006

(54) USE OF CARBOXY COMPOUNDS SUCH AS 2(4-ACETOXYPHENYL)2-CHLORO-N-METHYL-ETHYLAMMONIUM CHLORIDE AS ANTI-INFLAMMATORY AGENTS

(75) Inventors: Karolien De Bosscher, Zottegem (BE); Wim Vanden Berghe, Gentbrugge (BE); Guy Haegeman, Balegem (BE)

(73) Assignee: Gent Universiteit, Ghent (BE)

( * ) Notice: Subject to any disclaimer, the term of this patent is extended or adjusted under 35 U.S.C. 154(b) by 0 days.

(21) Appl. No.: 10/177,987

(22) Filed: Jun. 21, 2002

(65) Prior Publication Data

US 2003/0055030 A1 Mar. 20, 2003

Related U.S. Application Data

(63) Continuation of application No. PCT/EP00/13347, filed on Dec. 21, 2000.

(30) Foreign Application Priority Data

Dec. 21, 1999 (EP) .................................. 99204433

(51) Int. Cl.
- *A61K 31/22* (2006.01)
- *A61K 31/33* (2006.01)
- *A61K 31/21* (2006.01)
- *A61K 31/215* (2006.01)
- *A61K 31/135* (2006.01)

(52) U.S. Cl. ........................ 514/546; 514/183; 514/506; 514/529; 514/649

(58) Field of Classification Search ................ 514/183, 514/475, 506, 659, 546, 529, 649
See application file for complete search history.

(56) References Cited

U.S. PATENT DOCUMENTS

| 4,469,689 A | * | 9/1984 | Anderson et al. ........... 424/243 |
| 5,086,039 A | * | 2/1992 | Hammond ..................... 514/8 |
| 5,911,988 A | * | 6/1999 | Brownell et al. ........ 424/145.1 |

FOREIGN PATENT DOCUMENTS

| DE | 43 35 523 A1 | 10/1993 |
| GB | 1 600 639 | 5/1978 |
| JP | 02-032016 | * 2/1990 |
| WO | WO 98/14200 | 4/1998 |
| WO | WO 0145693 A1 | 12/2000 |

OTHER PUBLICATIONS

International Preliminary Examination Report, dated Apr. 5, 2002.
International Search Report, dated Feb. 27, 2001.
Louw et al., Mechanism for the Stabilization in Vivo of the Aziridine Precursor 2-(4-Acetoxyphenyl)-2-chloro-N-methyl-ethylammonium Chloride by Serum Proteins, Biochemical Pharmacology, 1997, pp. 189-197, vol. 53.

(Continued)

*Primary Examiner*—Shengjun Wang (74) *Attorney, Agent, or Firm*—Clark & Elbing (57) ABSTRACT

The present invention relates to the use of specific carboxy compounds, more specifically to the use of 2(4-acetoxyphenyl)-2-chloro-N-methyl-ethylammonium chloride, in the treatment of inflammatory diseases. Part of the invention is also a composition, preferably a pharmaceutical composition, comprising as active ingredient at least 2 (4-acetoxyphenyl)-2-chloro-N-methyl-ethylammonium chloride together with (pharmaceutically) acceptable excipients.

7 Claims, 6 Drawing Sheets

OTHER PUBLICATIONS

Louw et al., Influence of an Aziridine Precursor on the In Vitro Binding Parameters of Rat and Ovine Corticosteroid Globulin, Biochemical Pharmacology, Jan. 2000, pp. 167-175, vol. 59.

Louw et al., Salsola tuberculatiformis Botschantzev and an Aziridine Precursor Analog Mediate the in Vivo Increase in Free Corticosterone and Decrease in Corticosteroid-Binding Globulin in Female Wistar Rats, Endocrinology, May 1999, pp. 2044-2053, vol. 140, No. 5.

Swart et al., Inhibition of Cytochrome P-450 11-beta by Some Naturally Occurring Acetophenones and Plant Extracts from the Shrub salsola tuberculatiformis, Planta Medica, 1993, pp. 139-143, vol. 59, No. 2.

* cited by examiner

USE OF CARBOXY COMPOUNDS SUCH AS 2(4-ACETOXYPHENYL)2-CHLORO-N-METHYL-ETHYLAMMONIUM CHLORIDE AS ANTI-INFLAMMATORY AGENTS

CROSS-REFERENCE TO RELATED APPLICATION

This application is a continuation of International Application Number PCT/EP00/13347 filed on Dec. 21, 2000 designating the United States of America, International Publication No. WO 01/45693 (Jun. 28, 2001), the contents of the entirety of which is incorporated by this reference.

TECHNICAL FIELD

The present invention relates to the use of specific carboxy compounds, more specifically to 2(4-acetoxyphenyl)-2-chloro-N-methyl-ethylammonium chloride, to treat inflammatory diseases.

BACKGROUND

Synthetic glucocorticoids remain among the most effective agents for the treatment of chronic inflammatory diseases. However, major side effects severely limit their therapeutic use. Physiologic and therapeutic activities of glucocorticoids are mediated by a nuclear receptor belonging to a superfamily of ligand-inducible transcription factors that, in addition to directly regulating their cognate gene programs, can also interfere with other signalling pathways, such as those utilizing NF-κB.

NF-κB is an inducible transcription factor complex which regulates the expression of various genes involved in inflammatory and immune responses. It is activated upon exposure of cells to pro-inflammatory cytokines (TNF, IL-1), oxidants (hydrogen peroxide, ozone, superoxide anions), bacterial compounds (LPS), viral products (dsRNA, HTLV-I Tax protein), PKC activators (phorbol esters, platelet activating factor) and UV- or γ-irradiation.

NF-κB is a promising target for anti-inflammatory and immunosuppressive therapies. Inhibition of NF-κB activity by glucocorticoids (GC) has been well documented, although gene stimulatory effects by GC have also been observed.

Although GC remain, as mentioned above, among the most potent immunosuppressive and anti-inflammatory drugs currently available, and are especially effective in the treatment of chronic asthma or rheumatoid arthritis, side effects such as hypothalamic-pituitary-adrenal axis insufficiency, diabetes, altered lipid metabolism, steroid myopathy, osteoporosis, and infectious and neuropsychiatric complications limit the therapeutic use of classical glucocorticoid agonists. Therefore there is a need to investigate and search for novel compounds that have anti-inflammatory properties without having severe side-effects.

Compound A (CpdA) or 2-(4-acetoxyphenyl)-2-chloro-N-methyl-ethylammonium chloride is a stable analogue of the hydroxyphenylaziridine precursor found in the Namibian shrub Salsola tuberculatiformis Botschantzev (Louw, 1997). Contraceptive properties have been attributed to plants of the Salsola genus as early as 1902 and recognized and passed on through oral Bushman tradition (Brondegaard, 1973). Feeding experiments with the shrub indeed caused contraceptive effects in rats and prolonged gestation in sheep (van der Merwe, 1976; Basson, 1969). A study by van der Merwe et al. (1976) led also to the isolation of an active but very labile HPLC fraction from the dried plant material, a hydroxyphenylaziridine, and synthesis of a more stable but biologically active analogue, CpdA (Louw, 1997). Recent work performed by the group of Louw and co-workers set out to unravel the contraceptive mechanism of action and the molecular targets of this desert plant derivative analogue. Multiple levels of interference with endogenous glucocorticoid action were observed. From their results, it was concluded that CpdA disrupts the oestrus cycle of rats by interacting with glucocorticoid-binding proteins such as steroidogenic enzymes and plasma steroid-binding globulins, thereby altering the interaction between the hypothalamus, pituitary, adrenal gland and gonads (HPA axis versus HPG axis) (Louw, 1997 and 1999).

SUMMARY OF THE INVENTION

The present invention relates to the surprising finding that carboxy compounds such as CpdA display a specific anti-inflammatory effect to a similar extend as glucocorticoids without having the severe side effects of glucocorticoids.

BRIEF DESCRIPTION OF FIGURES

FIG. 12. L929sA cells are treated with either 1 μM DEX, 1 or 10 μM CpdA and/or 2000IU/ml TNF, where indicated. Cell lysates were made and activated JNK, p38 or ERK were detected using the corresponding phospho-specific MAPK antibodies (FIG. 12A, B and C respectively). The upper band in 12A is a nonspecific, constitutive band which actually serves as an additional loading control.

DETAILED DESCRIPTION OF THE INVENTION

The current invention concerns the use of a carboxy compound having the following formula (I) or its aziridine derivative as a medicament:

(I)

wherein R is a hydrogen or acyloxy group, X is a hydrogen, hydroxy or halogen such as chloride, bromide and fluoride and Y is a lower alkyl group such as methyl, ethyl, propyl and butyl. Preferably the R group is an acetoxy, X a halogen, most preferably a chloride, and Y a methyl.

The latter compounds can surprisingly be used as anti-inflammatory agents to treat inflammatory diseases. These compounds can also be used as agent to treat diseased states related to NF-κB- and/or AP-1-mediated gene expression.

The invention further relates to compositions, preferably pharmaceutical compositions, comprising as an active ingredient at least one of the compounds as defined in formula (I) together with (pharmaceutically) acceptable excipients. Unexpectedly, it appears that compounds having the formula (I), preferably those wherein the R group is an acetoxy, X is a halogen most preferably a chloride and Y is a methyl, demonstrate a strong inhibiting activity of NF-κB-driven genes, but exert a weak or no activity towards the glucocorticoid response element (GRE)-dependent genes. The preferred compound exerting this activity is 2(4-acetoxyphenyl)-2-chloro-N-methyl-ethylammonium chloride and has a molecular weight of 264.14. This compound is hygroscopic and sensitive to light; it should be kept in the freezer (–4° C.) and may not be exposed to light. This compound indeed starts to cyclise to the corresponding aziridine, when kept in solution (especially at pH5 and above) as described by Louw et al. 1997 (Biochem Pharmacol 24:167–75).

The term 'compound' (or 'drug-like compound') is well known to those skilled in the art and includes compounds suitable for use in medicine, for example as the active ingredient in a medicament. The compounds of the present invention can be purified from plants as indicated above but may also be synthesized by any known technique in organic chemistry, molecular biology or biochemistry. More specifically, the compounds of the present invention can be synthesized as described by Louw et al. 1997 (Biochem Pharmacol 24:167–75).

It is clear that the compounds of the present invention can also be used as "lead compounds". That is, they may provide a starting-point for the design of other compounds that may have other characteristics.

The compounds of the present invention have anti-inflammatory, analgesic and anti-pyretic activities comparable with glucocorticoids, but avoid side effects and are useful in methods of treating diseases or conditions in which NF-κB/IL6 have been implicated. Such diseases and conditions include those in which inflammation or tissue injury is involved such as osteoarthritis, rheumatoid arthritis, ankylosing spondylytis and other rheumatologic and pain indications. Other diseases in which inflammation is involved and in which the compounds of the present invention are useful include asthma, psoriasis, septic shock and inflammatory bowel disease. It is further believed that NF-κB is involved in diseases in which apoptosis is involved. As such, the compounds of the present invention are useful to limit tissue and/or cell damage and may be beneficial for ischaemic disease, neural injury and myocardial infarction. The compounds of the invention are useful in the treatment or prevention of Alzheimer's disease. They delay the onset or slowing the progression of Alzheimer's disease, even when used in low amounts.

The aforementioned compounds of the invention or compositions (formulations) thereof may be administered by any conventional method including oral and parenteral (e.g., subcutaneous, intraperitoneal, intravascular or intramuscular) injection. The treatment may consist of a single dose or a plurality of doses over a period of time.

Thus, the present invention involves a method of treating a subject having inflammation or an inflammation-related disorder with a therapeutically effective amount of a compound of the present invention. The invention is useful for, but not limited to, the treatment of inflammation in a subject, and for treatment of other inflammation-associated disorders such as pain, headaches or fever. As already indicated above, the compounds of the present invention are useful to treat arthritis, including but not limited to rheumatoid arthritis, spondyloarthritis, gouty arthritis, osteoarthritis, systemic lupus erythematosus, and juvenile arthritis. The compounds of the present invention are also useful in the treatment of asthma, bronchitis, menstrual cramps, tendinitis, bursitis, and skin related conditions such as psoriasis, eczema, acne, burns and dermatitis. Moreover, the compounds of the present invention are useful to treat gastrointestinal conditions, such as inflammatory bowel disease, Crohn's disease, gastritis, irritable bowel syndrome and ulcerative colitis and for the prevention or treatment of cancer, such as colorectal, breast cancer, prostate cancer or leukemia. The compounds of the present invention are further useful in treating inflammation in such diseases as vascular diseases, migraine headaches, periarteritis nodosa, thyroiditis, aplastic anemia, Hodgkin's disease, chronic lymphocytic leukemia, scleroderma, rheumatic fever, type I diabetes, myasthenia gravis, multiple sclerosis, sarcoidosis, nephrotic syndrome, Bechet's syndrome, polymyositis, gingivitis, hypersensitivity, swelling occurring after injury, myocardial ischemia and the like. In addition, the compounds of the present invention are useful in the treatment of ophthalmic diseases, such as retinitis, retinopathies, conjunctivitis, uveitis, ocular photophobia, and of acute injury to the eye tissue. The compounds of the present invention are also useful in the treatment of pulmonary inflammation, such as that associated with viral infections and cystic fibrosis. The compounds of the present invention are further useful for the treatment of certain central nervous system disorders such as cortical dementia including Alzheimer's disease. It should be stressed that the compounds of the present invention are useful as anti-inflammatory agents with the additional benefit of having significantly less harmful glucocorticoid side effects! Further, the compounds of the present invention may also be useful in the treatment of allergic rhinitis, respiratory distress syndrome, endotoxin shock syndrome, atherosclerosis and central nervous system damage resulting from stroke, ischemia and trauma. Besides being useful for human treatment, these compounds are also useful for treatment of mammals, including horses, dogs, cats, rats, mice, sheep, pigs, etc.

The phrase "therapeutically-effective" is intended to qualify the amount of agent for use in the therapy which will achieve the goal of improvement in inflammation severity and avoiding side effects typically associated with alternative therapies.

Also embraced within this invention are compositions comprising the compound of the present invention in association with one or more non-toxic, (pharmaceutically-acceptable) carriers and/or diluents and/or adjuvants (collectively referred to herein as 'excipients') and, if desired other ingredients. The active compounds and compositions may, for example be administered orally, intra-vascularly, intra-peritoneally, sub-cutaneously, intramuscularly or topically. For oral administration, the (pharmaceutical) composition may be in the form of, for example, a tablet, capsule, suspension, aerosol or liquid. The pharmaceutical composition is preferably made in the form of a dosage unit containing a particular amount of the active ingredient. Examples of such dosage units are tablets or capsules. The active ingredient may also be administered by injection as a composition wherein, for example, saline, dextrose or water may be used as a suitable carrier.

The amount of therapeutically active compounds that are administered and the dosage regimen for treating a disease condition with the compounds and/or compositions of this invention depends on a variety of factors, including the age, weight, sex and medical condition of the subject, the severity of the disease, the route and frequency of administration, and the particular compound employed, and thus may vary widely. The pharmaceutical compositions may contain active ingredients in the range of about 0.1 to 2000 mg, preferable in the range of about 0.5 to 500 mg and most preferably between about 1 and 100 mg. A daily dose of about 0.01 to 100 mg/kg body weight, preferably between about 0.5 and 20 mg/kg body weight and most preferably between about 0.1 to 10 mg/kg body weight, may be appropriate. The daily dose can be administered in one to four doses per day.

In the case of psoriasis and other skin conditions, it may be preferable to apply a topical preparation of compounds of this invention to the affected area two to four times a day.

For inflammation of the eye or other external tissues, e.g., mouth and skin, the formulations are preferable applied as a topical ointment or cream, or as a suppository, containing the active ingredients in a total amount of, for example 0.075 to 30% w/w, preferably 0.2 to 20% w/w and most preferably 0.4 to 15% w/w. When formulated in an ointment, the active ingredients may be employed with either paraffinic or a water-miscible ointment base. Alternatively, the active ingredients may be formulated in a cream with an oil-in-water cream base. If desired, the aqueous phase of the cream base may include, for example at least 30% w/w of a polyhydric alcohol such as propylene glycol, butane-1-diol, mannitol, sorbitol, glycerol, polyethylene glycol and mixtures thereof. The topical formulation may desirably include a compound which enhances absorption or penetration of the active ingredient through the skin or other affected areas. Examples of such dermal penetration enhancers include dimethyulsulfoxide and related analogs. The compounds of this invention can also be administered by a transdermal device. Preferably topical administration will be accomplished using a patch either of the reservoir and porous membrane or of a solid matrix variety. In either case the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane.

The oily phase of the emulsions of this invention may be constituted from known ingredients in a known manner. While the phase may comprise merely an emulsifier it may comprise a mixture of at least one emulsifier with a fat or an oil or with both a fat and an oil. Preferably, a hydrophilic emulsifier is included together with a lipophilic emulsifier that acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base that forms the oily dispersed phase of the cream formulations. Emulsifiers and emulsion stabilizers suitable for use in the formulation of the present invention include Tween60, Span80, cetostearyl alcohol, myristyl alcohol, glyceryl monostearate, and sodium lauryl sulfate, among others. The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredients are dissolved or suspended in suitable carrier, especially an aqueous solvent for the active ingredients. The anti-inflammatory active ingredients are preferably present in such formulations in a concentration of 0.5 to 20%, advantageously 0.5 to 10% and particularly about 1.5% w/w. For therapeutic purposes, the active compounds of this combination invention are ordinary combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosporic and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in dispersion of active compound in hydroxypropylmethylcellulose. Formulations for parental administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compound may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art. Although these compounds have been described with respect to specific embodiments, the details of these embodiments are not to be construed as limitations.

The invention is hereunder further explained by way of an 'Examples' section, without being restrictive in the scope of the current invention.

EXAMPLES

Materials & Methods

Cytokines and Reagents

Recombinant murine TNF, produced in our laboratory, has a specific biological activity of $1.3 \times 10^8$ units/mg protein and contained <1.8 ng endotoxin/mg protein. The specific activity was determined by a standardized cytotoxicity assay on 164 WEHI cl 13 cells compared with an international standard TNF preparation (National Institute for Biological Standards and Control, Potters Bar, UK). Dexamethasone was purchased from Sigma. A stock solution of the reagent was routinely prepared in dimethyl sulfoxide (DMSO) (Sigma-Aldrich) and stored at 4° C. The same procedure was followed for RU38486, which was described previously (Vanden Berghe et al., 1999). Staurosporine (STS) (Tamaoki et al., 1986; Ruegg et al., 1989) was purchased from Calbiochem-Novabiochem International (San Diego, CA) and was stored as a 2 mM solution in DMSO at −20° C.

Compound A or 2(4-acetoxyphenyl)-2-chloro-N-methyl-ethylammonium chloride has a molecular weight of 264.14. A stock solution was prepared in DMSO, aliquoted and stored at 4° C. in the dark.

Control experiments verified that the final concentration of organic solvent did not interfere with any of the assays.

The phospho-specific p38 (Thr-180/Tyr-182), p42/p44 (Thr-202/Tyr-204) and SAPK/JNK (Thr-183/Tyr-185) MAPK polyclonal rabbit antibodies detect only the dual phosphorylated form of MAPK. They were purchased from New England Biolabs (Beverly, Mass., USA) as part of a kit, which also includes anti-rabbit IgG coupled to horseradish peroxidase, used as a second antibody for Western blotting. Luciferase (luc) reagent comprised 270 µM CoA (Sigma), 470 µM luciferin (Sigma), and 530 µm ATP (Boehringer Mannheim) in 10 mM TRICINE, 0.54 mM $(MgCO_3)_4Mg(OH)_2$, 1.34mM $MgSO_4$, 0.05 mM EDTA, 16.7 mM DTT (all from Sigma).

Plasmids. p1168hu.IL6P-luc+, p1168(AP-1mut)IL6P-luc+, p1168(κBmut)IL6P-luc+ and p(IL6κB)$_3$50hu.IL6P-luc+ have been described previously (Plaisance, 1997; Vanden Berghe, 1998). pE-selectin-Luc was a kind gift from Dr. D. Goeddel (Tularik). pSVhGRα and pMMTV-Luc were a generous gift from Dr. W. Rombauts (Leuven). pNFκB-Luc was purchased from Stratagene Cloning Systems (La Jolla, Calif.). p(GRE)$_2$50hu.IL6P-luc+ was obtained by replacing the κB motifs in p(IL6κB)$_3$50hu.IL6P-luc+ with a linker region, containing two consensus GRE (underlined) sites flanked by a BglII and PstI restriction site. The following oligonucleotides were annealed: AGATCTCTCT-GCTGTACAGGATGTTCTAGCGGATCCT-GCTGTACAGGATGTTCTAGCTA CCTGCAG (SEQ ID NO:1) and TCTAGAGAGACGACATGTCCTACAA-GATCGCCTA GGACGACATGTCCTACAAG ATC-GATGGACGTC (SEQ IN NO: 2). The attached sequence listing is incorporated by this reference. The plasmids pGal4, pGal4-p65 and pGal4-VP16 were generously provided by Dr. M. L. Schmitz (DKFZ, Heidelberg). p(Gal)$_2$-50hu.IL6P-luc+ was previously described (De Bosscher, 1997).

The plasmids pGal4, pGal4-p65 and pGal4-VP16 were generously provided by Dr. M. L. Schmitz (DKFZ, Heidelberg). p(Gal)$_2$-50hu.IL6P-luc+ was previously described (De Bosscher, 1997).

Transfection Procedure

L929sA mouse fibroblast cells were stably transfected by the calcium phosphate precipitation procedure according to standard protocols (Graham et al., 1973; Vanhoenacker et al., 1994) using a 10-fold excess of the plasmid of interest over the selection plasmid pPGKβGeobpA. Transfected cells were selected in 500 µg/ml G418 for two weeks. Subsequently, resistant cell clones were pooled in order to level out individual clonal variation in expression and thus providing a reliable response upon induction. The cotransfected plasmid pPGKβGeobpA, conferring resistance to G418 and expressing constitutive P-galactosidase enzymatic activity, was further used as an internal control for calculating the protein concentration. L929sA cells were transiently transfected with the DEAE-dextran transfection method, essentially as described earlier (De Bosscher et al., 1997).

HEK293T human embryonic kidney cells were transiently transfected with the calcium phosphate precipitation technique. Briefly, $10^5$ actively growing cells were seeded in 24-well plates 24 hr before transfection and 400 ng of total DNA was transfected. 16 hr after transfection the medium was replaced with fresh medium, containing 5% fetal and 5% newborn calf serum (Life Technologies, Paisley, UK), containing the appropriate inducing agents. Cells were lysed with lysis buffer (TROPIX, Bedford, Mass.) and samples were assayed for their protein or β-galactosidase content and luciferase activity.

Reporter Gene Analysis

Luciferase assays were carried out according to the instructions of the manufacturer (Promega Biotech). Light emission was measured in a luminescence microplate counter (Top-Count; Packard Instrument Co., Meriden, Conn.). Luciferase activity, expressed in arbitrary light units, was corrected for the protein concentration in the sample by normalization to the co-expressed β-galactosidase levels. β-galactosidase protein levels were quantified with a chemiluminescent reporter assay Galacto-Light kit (TROPIX, Bedford, Mass.). Promoter activities are expressed as relative 'induction factor', i.e. the ratio between the expression levels of induced versus the non-induced state, with the latter taken to be 1.

Cell Culture $10^5$ cells were plated out in 24-well plates and inductions were done at least in triplicate for each independent experiment, which was carried out twice. Inductions with DEX or CpdA at the indicated concentrations were added at −2h for a total of 8h, while TNF (2000 IU/ml) or STS (60 nM) was added at time point zero and left on the cells for 6 h.

Lysates were made by washing the cells once with PBSA followed by addition of 100 µl of lysis buffer (TROPIX, Bedford, Mass.) per 24-well. Luciferase and µ-galactosidase levels were measured as stated above.

IL-6 ELISA. A murine IL-6 ELISA was performed by using a kit and the assay was performed according to the manufacturer's instructions (R&D systems, UK). By making a standard graph, OD measurements could be correlated with levels of IL-6 present in the supernatant of the induced cells. IL-6 levels were expressed in pg/ml. EMSA. An electrophoretic mobility-shift assay or EMSA was performed essentially as previously described (De Bosscher et al., 1997). DNA-binding activity was tested with an oligonucleotide containing the NF-κB site which comprises the sequence 5'-AGCTATGT GGGATTTTCCCATGAGC-3' (SEQ ID NO: 3) (underlined: single κB motif derived from the IL-6 promoter). DEX (1 µM) and CpdA (1 and 0.1 µM) were added 2 hours before TNF (2000 IU/ml). For supershift assay, 1 µl polyclonal anti-p65 antibody from Santa Cruz (Santa Cruz Biotechnology, Santa Cruz, Calif.) was added to the binding reaction.

MAPK activation assay.

The assay was performed essentially as described by Boone et al., 1998. Briefly, L929sA cells were seeded at 250.000 cells/well in 6-well plates. After 24 h, cells were either left untreated, or treated with 1 µM DEX or with CpdA (1 or 10 µM, as indicated on the figure) for 2 h and/or 2000 IU/ml TNF for 15 minutes. At the end of the incubation period, cells were washed in PBS. Cell extracts were essentially prepared as described in the protocol of a PhosphoPlus p38 MAPK antibody kit (New England Biolabs). One fifth of the total cell lysate (20 µl ) was separated by 12% SDS-PAGE and blotted onto a nitrocellulose membrane. Western blot analysis was performed to detect phosphorylated MAPK proteins.

Example 1

CpdA Transrepresses TNF-Induced IL-6 Promoter Activity

Figure 1:
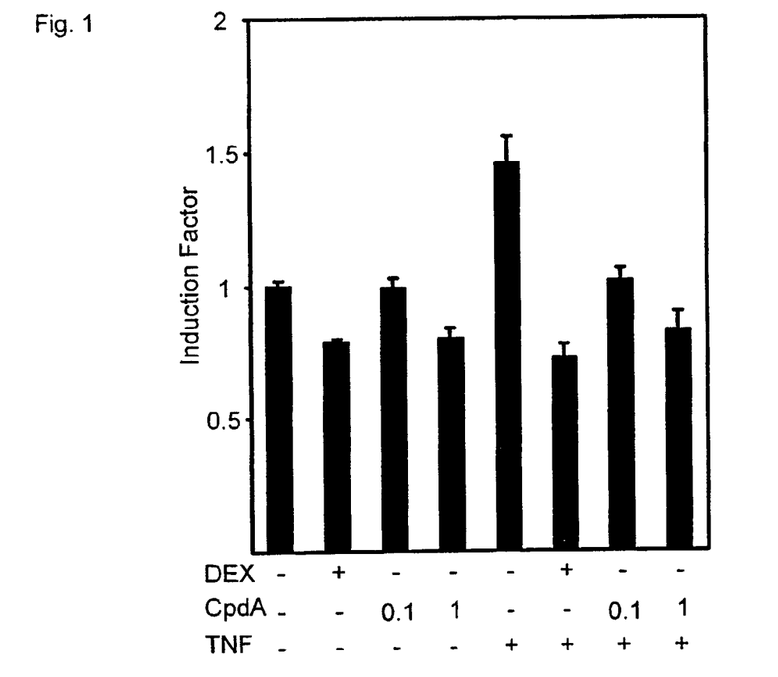
FIG. 1. L929sA cells with the stably integrated reporter gene construct p1168hu.IL6P-luc+ were either treated with 1 µM of DEX, 0.1 or 1 µM of CpdA, as indicated, in absence or presence of 2000 IU/ml TNF. DEX or CpdA was added 2 hours before TNF for a total induction period of 8 hours. Cell lysates were assayed for luc activities and normalized for protein content. Promoter activities are expressed as 'induction factor', i.e. the ratio of expression levels recorded either under induced and non-induced conditions. Assays were performed in triplicate and results are representative of at least two independent induction experiments.

In order to investigate whether the inhibitory action of CpdA is directed at the transcriptional level of IL-6 gene induction, we tested the effect of CpdA on an IL-6 promoter-driven reporter gene construct. FIG. 1 shows that the induction with TNF of a p1168hu.IL6P-luc+ construct stably integrated in L929sA cells, can efficiently be inhibited with 1 µM of DEX. A downmodulatory effect of CpdA at 0.1 µM is already apparent, while a 1 µM concentration of CpdA in combinaton with TNF lowers the relative luciferase induction factor to almost the same extent as 1 µM DEX.

Example 2

CpdA Inhibits a STS-Induced AP-1-Driven IL-6 Promoter Variant

Figure 2:
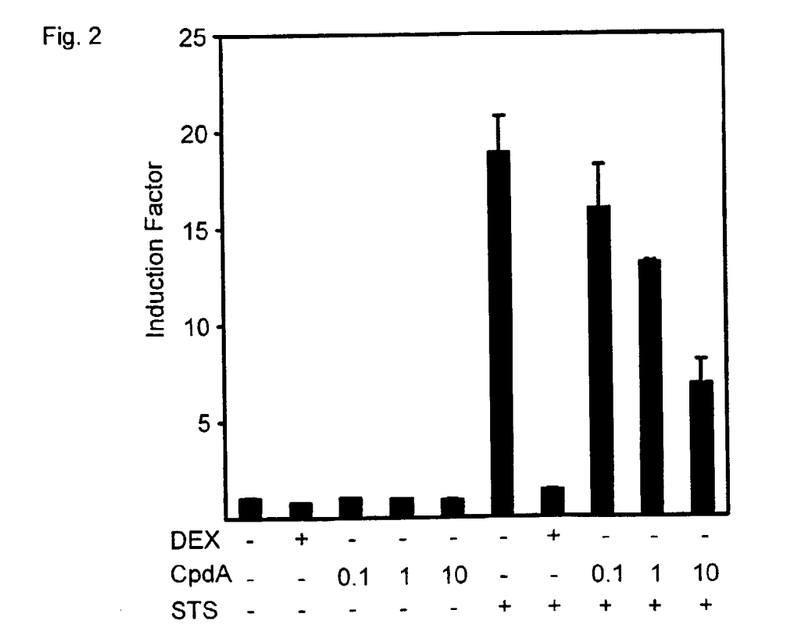
FIG. 2. L929sA cells with a stably integrated p1168 (κBmut)IL6P-luc+ construct were either treated with 1 µM DEX, 0.1, 1 or 10 µM CpdA, in absence or presence of 60 nM Staurosporine (STS). Induction protocol and plotting of the results is similar as in FIG. 1.

Glucocorticoids can also exert transrepression of AP-1-driven genes. To see whether the inhibitory action of CpdA can also be directed to AP-1 activity, the κB-site of the IL-6 promoter was mutated. For this promoter variant, previous results have shown a complete loss of inducibility by TNF (Vanden Berghe et al., 1998, J.Biol.Chem, 273, 3285–3290). For this reason, the effect of CpdA on STS-induced promoter activity was examined. FIG. 2 shows that STS can strongly activate a p1168(κBmut)IL6P-luc+ construct, stably integrated in L929sA cells, and that DEX at 1 µM efficiently inhibits the AP-1-mediated transactivation. CpdA is also capable of inhibiting the STS-induced transactivation at concentrations of 0.1, 1 and 10 µM.

Example 3

Figure 3:
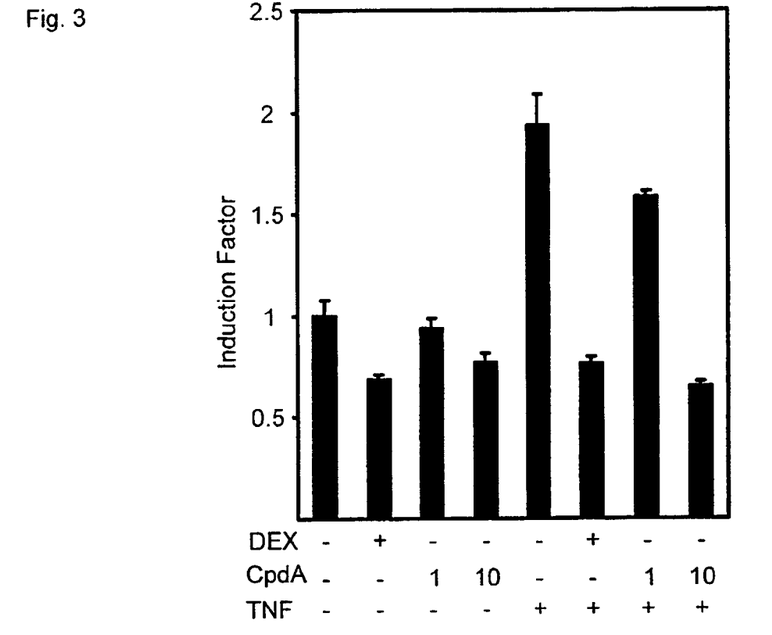
FIG. 3. L929sA cells with the stably integrated reporter gene construct p1168(AP-1-mut)IL6P-luc+ were either treated absence or presence of 2000 IU/ml TNF. DEX or CpdA was added 2 hours before TNF for a total induction period of 8 hours. Induction protocol and plotting of the results is similar as in FIG. 1.
Figure 4:
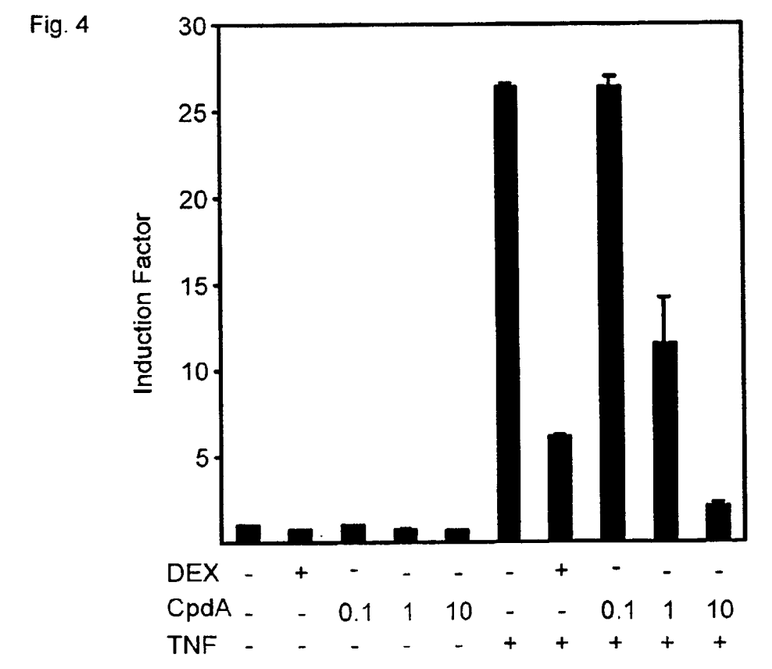
FIG. 4. L929sA cells with the stably integrated reporter gene construct p(IL6κB)₃50hu.IL6P-luc+ were either treated with 1 µM of DEX, 0.1, 1 or 10 µM of CpdA, as indicated, in absence or presence of 2000 IU/ml TNF. DEX or CpdA was added 2 hours before TNF for a total period of 8 hours. Induction protocol and plotting of the results is similar as in FIG. 1.

CpdA Transrepresses TNF-Induced IL-6 Promoter Activity Via negative Interference with the Transcription Factor NF-κB Previous studies in our group have designated NF-κB as the most important transcription factor involved in TNF-mediated IL-6 gene induction. However, TNF induction of the IL-6 promoter activates not only NF-κB, but also AP-1. To rule out the additional effect of TNF on AP-1 activity and to investigate the actual transcription factor target of CpdA, the AP-1 binding site was mutated. FIG. 3 shows that TNF activates a p1168(AP-1mut)IL6P-luc+ construct stably integrated in L929sA cells, and that DEX at 1 µM can efficiently inhibit this NF-κB-mediated transactivation. Again, CpdA at concentrations of 1 µM and 10 µM is capable of significantly inhibiting the TNF-induced promoter activity. FIG. 4 shows that CpdA inhibits, to a similar extent as DEX, the TNF-activated recombinant reporter gene construct p(IL6κB)$_3$ 50hu.IL6Pluc+.

Example 4

CpdA Downregulates TNF-Induced E-Selectin Promoter Activity

Figure 5:
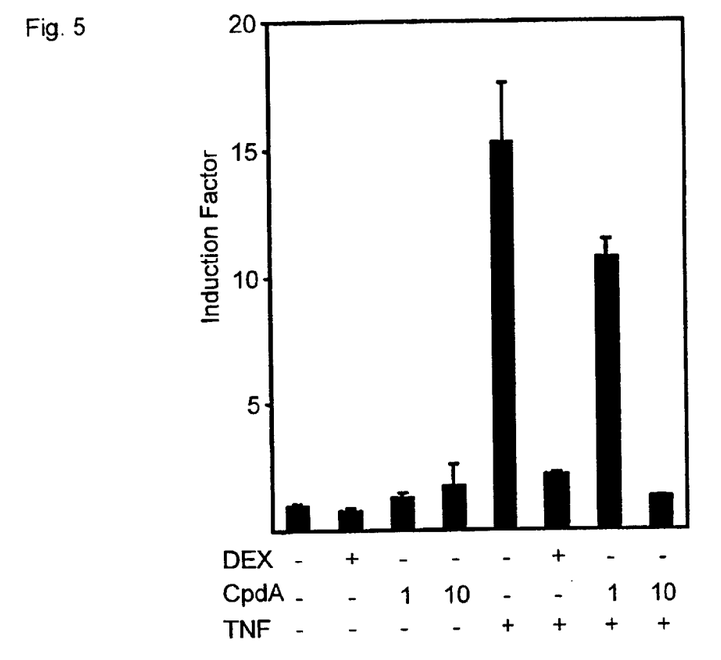
FIG. 5. L929sA cells with a stably integrated pE-selectin-Luc construct were either treated with 1 µM DEX, 1 or 10 µM CpdA, in absence or presence of 2000 IU/ml TNF. Induction protocol and plotting of the results is similar as in FIG. 1.
Figure 6:
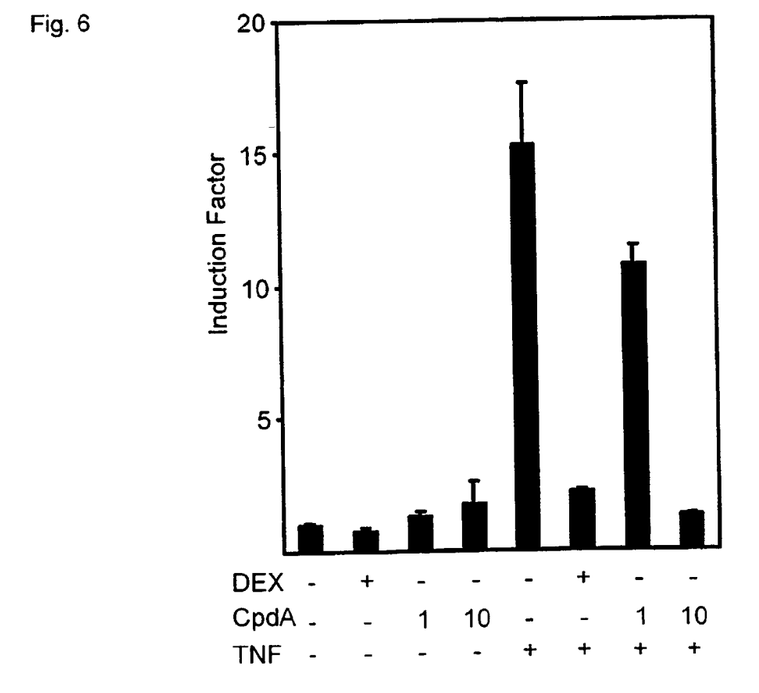
FIG. 6. L929sA cells with a stably integrated pICAM-Luc construct were either treated with 1 µM DEX, 1 or 10 µM CpdA, in absence or presence of 2000 IU/ml TNF. Induction protocol and plotting of the results is similar as in FIG. 1.

The downregulatory effect of CpdA was investigated on other physiological promoters, such as of the E-selectin and ICAM genes. FIG. 5 demonstrates that CpdA-mediated inhibition can also be demonstrated on TNF-induced pE-selectin-luc+, stably integrated in L929sA cells. CpdA at 10 µM inhibits the TNF-activated reporter to the same extent as 1 µM DEX, i.e. to background levels. 1 µM CpdA in combination with TNF is also effective, though to a lesser extent. Similar results were obtained with the ICAM promoter (FIG. 6).

Example 5

CpdA Exhibits No Transactivation Potential on a GRE-Dependent Reporter Gene

CpdA demonstrates a similar transrepressive action on NF-κB and AP-1-driven genes as glucocorticoids. We were interested to know whether CpdA mediates these effects by binding to and modulating the glucocorticoid receptor in the same manner as the steroidal ligand, DEX. Hereto we investigated whether CpdA can stimulate a GRE-driven promoter coupled to luciferase.

Figure 7:
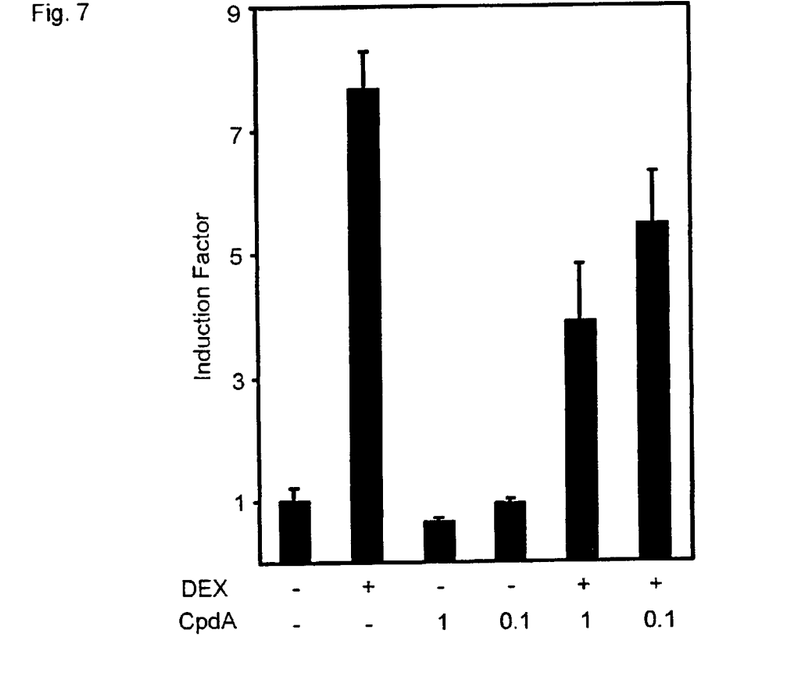
FIG. 7. L929sA cells with a stably integrated p(GRE)₂-50-luc+ construct were induced with 1 µM DEX, in absence or presence of 0.1 or 1 µM CpdA for a total induction period of 8 hours. Plotting of the results is similar as in FIG. 1.

FIG. 7 demonstrates the lack of activity of CpdA at 0.1 and 10 µM on a p(GRE)$_2$-50-luc+ construct, stably integrated in L929sA cells. In contrast, DEX is able to transactivate this construct at least 8-fold. Stimulation with both agents together indicates competition for GR molecules present in the cell.

Example 6

CpdA Inhibits TNF-Induced IL-6 Protein Production

Corticosteroids exert their anti-inflammatory action by downmodulating the expression of pro-inflammatory genes. We were interested to know if CpdA could repress the pro-inflammatory cytokine IL-6 as compared to dexamethasone, a synthetic steroid ligand for GR.

Figure 8:
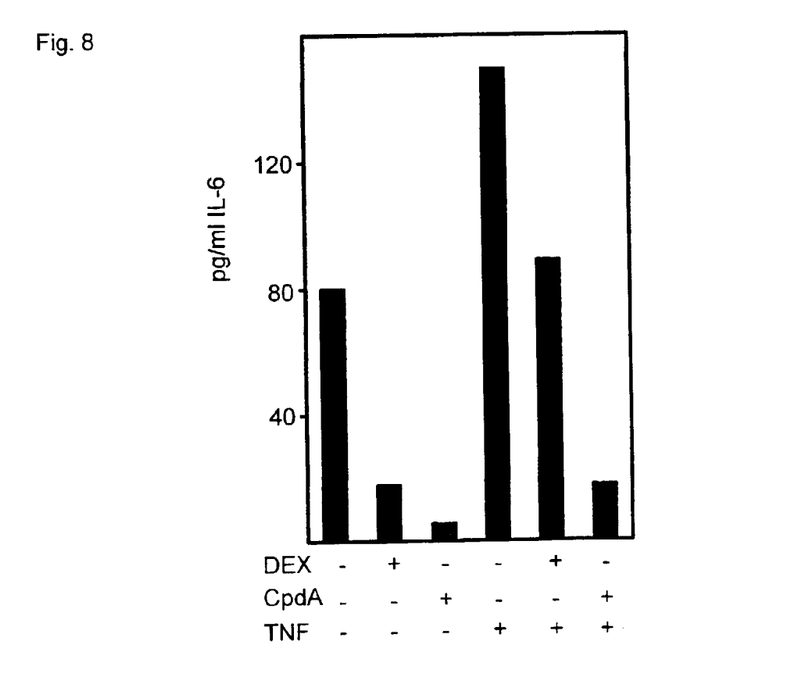
FIG. 8. A murine IL-6 ELISA was performed using the supernatant culture medium of subconfluent induced cells. Cells were treated with 1 μM DEX or 10 μM CpdA, in absence or presence of 2000 IU/ml TNF. DEX or CpdA was added 2 hours before TNF, for a total induction period of 8 hours. This figure is representative of two independent experiments.

FIG. 8 shows that TNF is able to stimulate endogenous murine IL-6 production in L929sA cells, and that CpdA at 1 µM and at 10 µM is able to efficiently lower these TNF-induced levels.

Example 7

Figure 9:
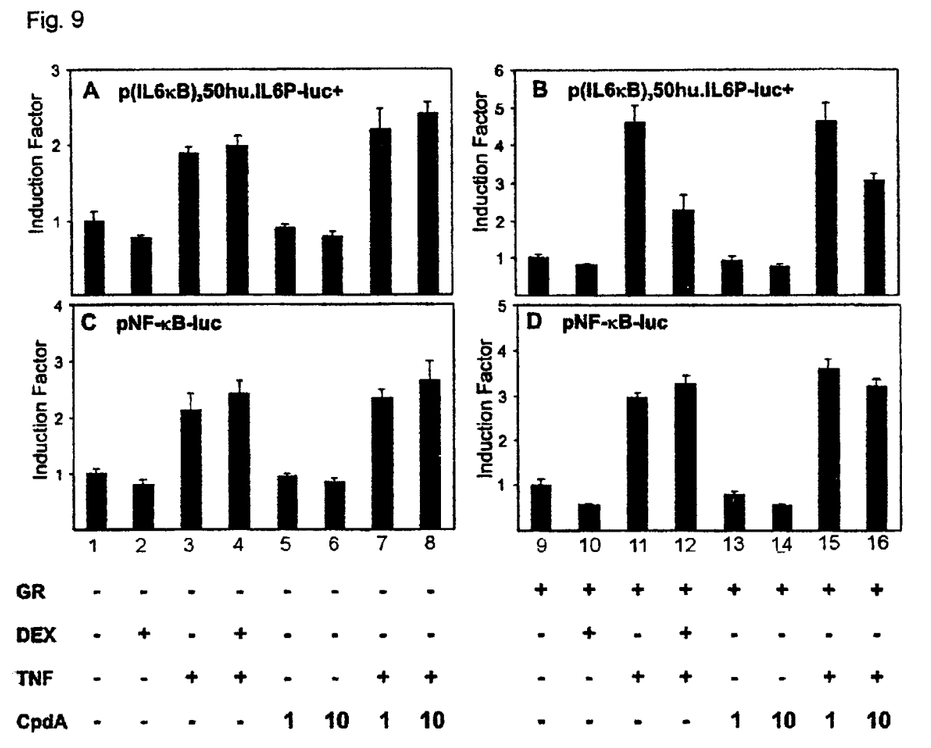
FIG. 9. A to D. HEK293T cells were transiently transfected with 100 ng of p(IL6kB)350hu.IL6P-luc+ (A and B) or pNF-kB-Luc (C and D), 100 ng of a β-Galactosidase control plasmid and 200 ng of Mock DNA (A and C) or pSVhGRa (B and D). After transfection, cells were pre-incubated for 2 hours with 1 μM DEX and 10 μM CpdA and RU486, where appropiate. Subsequently, TNF (2000 IU/ml) was added, where necessary, and inductions were continued for another 6 hours. Plotting of the results is as described for FIG. 1, except that the non-induced state is taken as 100.

CpdA Repression of NF-κB-Driven Genes is Dependent on the Presence of GR and the Constitution of the TATA-Box In HEK293T cells the amount of endogenous GR is negligable, therefore, we used these cells to test whether the effect of CpdA depends on the presence of GR. FIG. 9 (panel A and B) demonstrates that, only when GR is present, TNF-activated p(IL6-κB)$_3$50hu.IL6P-luc+ can be repressed by DEX and CpdA (compare lanes 4 and 8 of panel A with lanes 12 and 16 of panel B). This result represents evidence that CpdA does work via the activated GR. Previously we have observed that glucocorticoid repression is dependent on the identity of the TATA box. We found that a NF-κB-Luc construct carrying an E1B TATA could be activated by TNF, but no longer showed responsiveness to GC repression, however, the molecular mechanism behind this remarkable phenomenon is not known yet. We were interested to find out whether CpdA repression was also influenced by the TATA box context.

Interestingly, similarly as observed with DEX, also CpdA is not able to mediate repression of pNF-κB-Luc, suggesting CpdA and DEX work via a similar mechanism. (FIG. 9, panel C and D).

Example 8

CpdA Does Not Interfere with the DNA-Binding Activity of NF-κB

Figure 10:
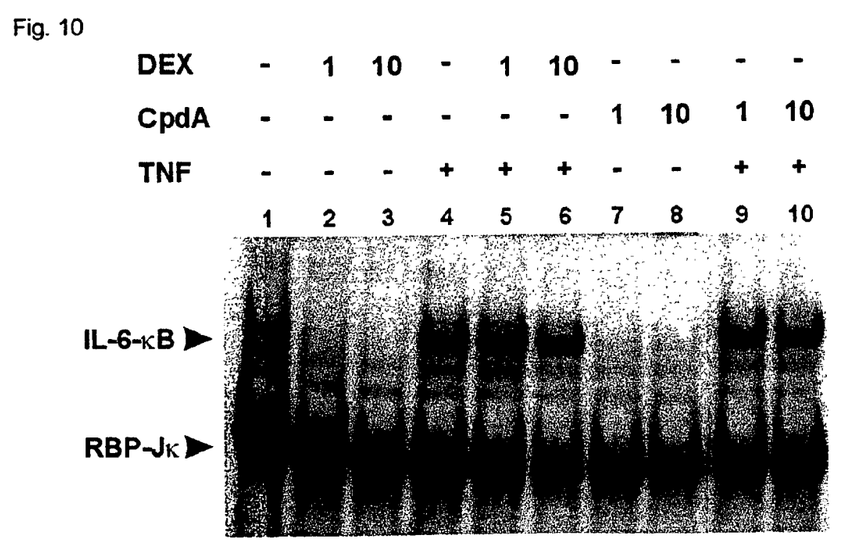
FIG. 10. L929sA cells were either left untreated or treated with DEX (1 μM) and various concentrations of CpdA, as indicated (in μM), alone or together with TNF (2000 IU/ml). DEX and CpdA were added 2 hours before TNF, for a total period of 4 hours. The total protein extract was incubated with a 32P-labeled IL-6 NF-κB response element and protein-DNA complexes were analyzed in an EMSA. Arrowheads indicate the activated κB complex, the constitutively expressed recombination binding protein (RBP)-Jκ and the free probe. Composition of NFκB complexes has been described in detail in (Vanden Berghe et al., 1999 J Biol. Chem. 274: 32091–32098, Plaisance et al., 1997 Mol. Cell. Biol. 17: 3733–3743).

The mechanism of action by which CpdA inhibits NF-κB-driven gene expression can take place at several levels. Previously, we demonstrated that in L929sA cells DEX represses NF-κB-driven genes without affecting the DNA-binding capacities of NF-κB. Since some effects of CpdA are reminiscent of GR-mediated gene repression, we investigated the effect of CpdA on NF-κB DNA-binding activity. FIG. 10 shows however that also for CpdA no change of NF-κB DNA-binding activity is observed at all concentrations indicated. Similar results were obtained for TC10 mouse endothelial cells (data not shown).This result suggests that the repressive mechanism of CpdA is not effected by abolishing the NF-κB DNA-binding activity and lets presume a mechanism reminiscent of that published for GC-mediated repression of IL-6-driven genes (De Bosscher, 1997).

Example 9

CpdA Inhibits the Transactivation Potential of p65

Figure 11:
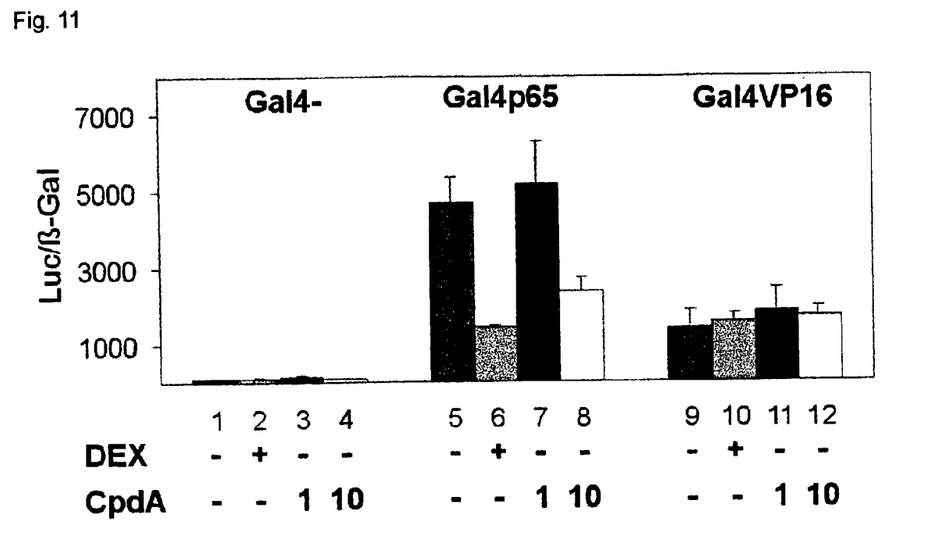
FIG. 11. L929sA cell lines with various stably transfected Gal4 constructs, as indicated in the graph, were transiently transfected with the p(Gal)$_2$-50hu.IL6P-luc+ reporter gene. After transfection, cells were either left untreated or treated with DEX (1 μM) and various concentrations of CpdA, as indicated (in μM).

Our previous data demonstrated that glucocorticoids mediate transrepression of NF-κB via a nuclear interference mechanism between this transcription factor and the activated GR (De Bosscher, 1997). Since CpdA, similar to DEX, does not affect the DNA-binding activity of NF-κB, we tested its effect on the transactivation capacities of p65, by making use of a Gal4-p65 chimeric protein. This fusion protein stimulates a gal4-dependent reporter gene. FIG. 11 demonstrates that DEX as well as CpdA at 10 µM is able to halfmaximally inhibit the activity of Gal4p65. Specificity of repression is demonstrated by using Gal4 fused to the viral activator VP16 as a negative control.

Example 10

CpdA Does Not Inhibit JNK Kinase Activity

Figure 12:
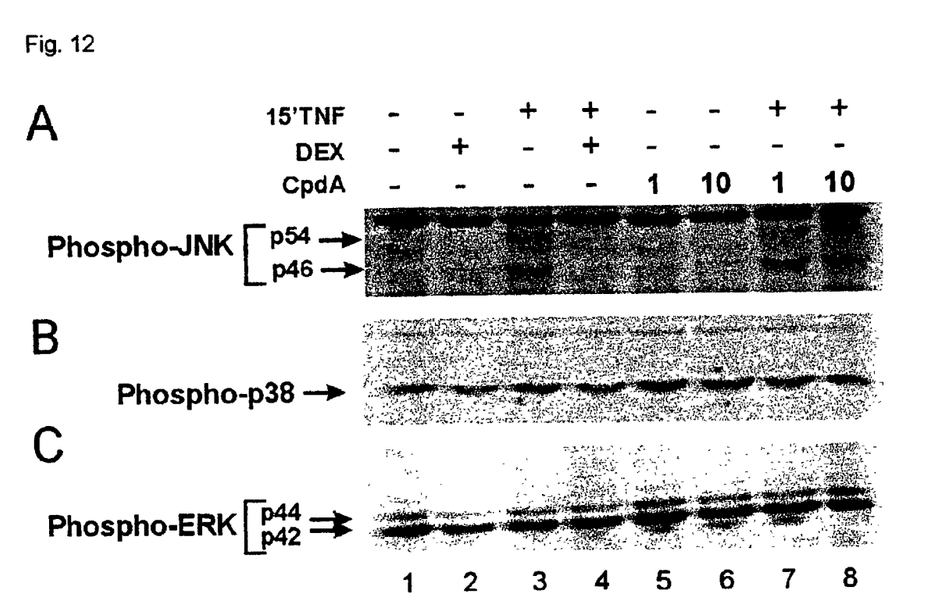

It has been reported that part of the mechanism by which GC can mediate gene repression of AP-1-driven genes is by inhibiting the JNK kinase activity. DEX is able to prevent phosphorylation and subsequent activation of JNK, at its turn unable to phosphorylate the c-Jun component of AP-1 (Caelles, 1997). Our aim was to find out whether CpdA could also inhibit activated MAPK, in a similar way as DEX. We performed MAPK assays with lysates from L929sA cells and this lead to the following interesting results (FIG. 12). Unlike DEX, which is able to inhibit the amount of phosphorylated JNK, CpdA does not affect the amount of activated JNK p46 and p54. The amount of activated, phosphorylated p38 and ERK MAPK kinases was not affected by either DEX or CpdA. From this result we can conclude that CpdA does not mediate AP-1-dependent gene repression by interference with the JNK kinase pathway.

Example 11

11.1 Beneficial Activities of CpdA in Cotton-Pellet Granuloma and Croton Oil-Induced Ear Oedema Test The anti-inflammatory activities of CpdA are evaluated in two animal models, the cotton-pellet granuloma test performed with female Wistar rats and the croton oil-induced ear oedema test with mice.

The cotton-pellet granuloma assay is performed as described by Meier R et al. (1950: Experientia 6:469–477), Vayssiere BM et al. (Mol Endocrinol. 1997 August; 11(9): 1245–55) and Vanden Berghe W et al. (Mol Pharmacol.

October 1999; 56(4): 797–806). Two cotton pellets (10 mg each) are inserted subcutaneously into the upper dorsal area of female Wistar rats (weight range 90–100 g, Iffa Credo, France). Test compounds are administered orally once a day for 4 days. Twenty-four hours after the last treatment, the animal is killed and the pellet, along with the surrounding granuloma, is carefully dissected from the animal and its dry weight is determined. For this, granuloma and pellet are heated at 60° C. overnight. By subtracting the initial weight of the pellet, the dry weight of the granuloma is determined. The anti-inflammatory potential of the compounds is evaluated by their ability to prevent granuloma formation and expressed as the compound doses at which the granuloma formation is decreased by 50% (ED50, given in milligrams/kg) estimated from dose-response curves. In the same test, the thymus is removed, and thymolysis is measured. The CpdA doses needed to obtain 50% reduction of the thymus weight (ED50) are given in milligrams/kg.

The croton oil-induced ear oedema test is carried out as described by Tonelli G et al 1965 (Endocrinology 77:625–634), Vayssiere BM et al. (Mol Endocrinol. August 1997; 11(9):1245–55) and Vanden Berghe W et al. (Mol Pharmacol. October 1999; 56(4): 797–806) on groups of eight male OF1 mice weighing 18–22 g (Iffa Credo, L'Arbresle, France). Oedema is induced on one ear by the application of a solution of croton oil (2% vol/vol) in pyridine-water-ether 4:1:14.6 (by volume). Animals are killed 6 h later, and the ears are removed and weighed. Edema is determined from the difference in weight between the irritant-treated and the contra-lateral ear. The compound to be tested is dissolved in the croton oil solution and topically applied on the ear during 6 hours. ED50 values correspond to the doses reducing the control edema by 50%. The ED50 values are expressed in micro-grams/ ear.

11.2. Beneficial Effects of CpdA in Autoimmune Disease Models in Mice

Experimental autoimmune disease mice models for encephalomyelitis (EAE)), uveitis (EAU), collagen-II arthritis (CIA), thyroiditis, nephritis, myasthenia gravis, orchitis, lupus, diabetes and osteoarthritis as described in detail by Matthys P et al. (J Leukoc Biol. Oct. 2000; 68(4):447–54), Matthys P et al (J Immunol. Oct. 15, 1995; 155(8):3823–9), Matthys P et al. (Eur J Immunol. September 1993; 23(9): 2209–16), Eynon EE et all (Immunol Rev. June 1999; 169:5–10) and Kollias G et all. (Immunol Rev. June 1999; 169:175–94) are being used to test the beneficial effects of CpdA in autoimmune disease. CpdA is administered systemically (iv or ip) and/or locally (intra-articular) by injection. In case of low stability/rapid clearance of the active compound, a peristaltic pump is used for obtaining a continuous flow and an accumulation of CdpA at the specific tissue under investigation. Cpd A is administered at a dose preferably 10 times more concentrated than the prednisolone, most preferably in the same dose range as described in detail in Alegre et al. (J. Immunol. 1991, vol 146, p. 1184).

11. 3. Beneficial Effects of Cpd A on TNF Lethality Models in Mice

Female C57Bl/6 mice (Charles River, Sulzfeld, Germany), eNOS-deficient mice (Huang et al., Nature 1995, vol 377, p. 239–242), or iNOS-deficient mice (Laubach et al., Proc. Natl. Acad. Sci. USA, 1995, vol 92, p. 10688–10692) (Jackson Laboratories) are being used at the age of 7–12 weeks at the beginning of the experiment. The animals are housed in temperature-controlled, air-conditioned facilities with 12 hr dark/ light cycles and food and water ad libitum. All experiments are approved by and performed according to the guidelines of the animal ethics committee from the Universities of Ghent, Belgium, and Maastricht, The Netherlands. Four different TNF lethality models are used. In model I, a lethal dose of mTNF is injected i.v. in healthy, non-sensitized mice. The sensitization models II, III, and IV are performed as described in detail before (Cauwels et al., J. Immunol. 1995, vol 154, p. 2753–2763; J. Immunol. 1996, vol 156, p. 4686–4690). Briefly, in model II mice bearing an i.m. LLCH61 tumor with a diameter of about 15 mm are challenged with 20 µg hTNF, while in model III mice are sensitized by a BCG infection 2 weeks before being challenged by a 10–15 µg hTNF injection. Model IV consists of a daily i.p. treatment with 1 µg rmIL-12 during 5 consecutive days, followed after a 2 day interval by a lethal hTNF challenge of 5–10 µg. All TNF injections are performed i.v. (200 µl, diluted in endo- toxin-free PBS) and 100% lethal. The LD100 is determined with exactly the same lot of TNF and mice before the start of each individual experiment. Lethality is generally scored up to 7 days after TNF challenge. Cytokines, cell lines, and the reagents recombinant hTNF, mTNF, and mIFNg are produced in *Escherichia coli* and purified to homogeneity in our laboratory. The endotoxin content is 0.02 ng/mg, as assessed by a chromogenic Limulus amoebocyte lysate assay (Coatest; Kabivitrium, Stockholm, Sweden). Live BCG organisms are provided by the Institut Pasteur du Brabant (Brussels, Belgium), and recombinant mIL-12 is generously provided by Dr. M. Gately (Hoffmann-La Roche, Nutley, N.J.). Murine LLC clone H61 and the B16BL6 melanoma subline are gifts from Dr. M. Mareel (University Hospital, Ghent, Belgium) by courtesy of Dr. G. Vaes and Dr. I. Fidler, respectively. Tumor cells are cultured in DMEM supplemented with 10% FCS, 50 U/ml penicillin G, 50 mg/ml streptomycin sulfate, and 2 mM L-glutamine. Before injection, cells are washed twice in PBS. Cpd A is injected i.v. at a dose preferably 10 times more concentrated dose range of prednisolone, most preferably in the same dose range. CpdA is dissolved in solution suitable for i.v. injection. Injection solutions are diluted in endotoxin-free PBS, and, unless stated otherwise, injection volumes are 200 µl. CpdA is administered systemically (iv or ip) or locally (intra-articular) by injection. In case of low stability/rapid clearance of the active compound, use of peristaltic pump is beneficial for continuous flow and accumulation of the latter compound at tissue under investigation. Cpd A is administered at a dose preferably 10 times more concentrated than prednisolone, most preferably in the same dose range as described in detail by Alegre et al. (J. Immunol. 1991, vol 146, p.1184). More details of the above-described experiment can be found in Cauwels et al (Immunity. August 2000; 13(2):223–31), Freeman BD & Natanson C. (Expert Opin Investig Drugs. July 2000; 9(7): 1651–63), Meduri GU. (J Chemother. December 1999; 11(6):541–50), and Kollias et al. (Immunol Rev. June 1999; 169:175–94).

11.4. Beneficial Effects of Cpd A in Acute and Colitis Mice Models

Experimental mice models as described in detail by Steidler, L., W. Hans, et al. (2000, Science 289(5483): 1352–5), Bhan et al. (Immunol Rev. June 1999; 169:195–207), Aranda et al. (J Immunol 158(7): 3464–73), Berg, D. J. & N. Davidson, et al. (1996, J Clin Invest 98(4): 1010–20), Kojouharoff, G., W & Hans, et al. (1997, Clin Exp Immunol 107(2): 353–8), Kuhn, R., J. Lohler, et al. (1993, Cell 75(2): 263–74), Okayasu, I., S. Hatakeyama, et al. (1990, Gastroenterology 98(3): 694–702) and/or Powrie, F., R. L. Coffman, et al. (1994, Res Immunol 145(5): 347–53) are used in the present experiment.

Cpd A is administered at a dose preferably 10 times more concentrated than prednisolone, most preferably the same dose range as described in Steidler, L., W. Hans, et al. (2000, Science 289(5483): 1352–5)

11.5. Beneficial Effects of Cpd A in Liver Shock Model (Hepatitis Model)

An experimental shock model as described in detail in Van Molle et al. (Infect Immun. September 2000; 68(9): 5026–9) and Hochepied et al. (J Biol Chem. May 19, 2000; 275(20):14903–9) is used in the present experiment. Female C57BL/6 mice (Iffa-Credo, Saint Germain-sur-l'Arbresle, France) are used at the age of 8–12 weeks. Rat a 1-AGP transgenic mice were generated as described below. They were generated by injecting genomic DNA into (C57BL/6 3 DBA/2)F1 zygotes, and the resulting transgenic mice are back-crossed eight generations into a C57BL/6 background. Heterozygous transgenic mice from the line 9.5–5 constitutively produce about 2 mg/ml a 1-AGP. This is 10-fold more than wild-type (wt) animals. The colony was propagated by breeding heterozygous transgenic mice with C57BL/6 female mice; the offspring, containing heterozygous transgenics and wt littermates, was genotyped at weaning age by enzyme-linked immunosorbent assay. 100 µl of blood was co which serum was prepared. A 1-AGP was purified by phenol extraction and coated on the bottom of an enzyme-linked immunosorbent assay plate. After washing, rat a 1-AGP is detected using an anti-rat a 1-AGP polyclonal antibody (generated by H. Baumann in rabbits) (1/1,000) and an anti-rabbit antibody, conjugated to alkaline phosphatase (Sigma, St. Louis, Mo.; 1/5,000). The anti-rat a 1-AGP antibody does not cross-react with mouse a 1-AGP. About 50% of the offspring are heterozygous transgenic. Only female mice of 8–12 weeks are used in the experiment. Both transgenic and control (nontransgenic littermate) mice have comparable body weights. Mice are kept in a conventional, air-conditioned mouse room in 12-h light-dark cycles and recieved food and water ad libitum. Intraperitoneal injections have a volume of 0.5 ml. The reagents are diluted in pyrogen-free phosphate-buffered saline (PBS) immediately before injection. Mice are injected intramuscularly with bacteria (right thigh) in a volume of 100 µl. Mice are bled by retro-ocular bleeding or heart puncture under ether or tribromoethanol (160 mg/kg) anesthesia, respectively, and serum was prepared by clotting 30 min at 37° C., removal of the clot, and centrifugation (15 min at 15,000 g). Bovine a 1-AGP, bovine serum albumin (BSA), alkaline phosphatase-conjugated anti-rabbit IgG, and p-nitrophenyl phosphate are obtained from Sigma. The a 1-AGP preparations contain 10 ng of endotoxin/mg of protein. a 1-AGP was 99% pure as mentioned by the manufacturer and as judged by polyacrylamide gel electrophoresis and subsequent Coomassie Blue staining. Recombinant mouse IL-1b was expressed in and purified from *E. coli* in our laboratory, had a specific activity of $3.65 \cdot 10^8$ units/mg, and contained less than 10 ng of endotoxin/mg of protein. *K. pneumoniae* (ATCC 43816), a strain that produces a lethal infection in normal mice, is inoculated in the right thigh muscle as described. An inoculum of $1-3 \cdot 10^6$ CFU/mouse is used except in the studies with rat a 1-AGP transgenic mice, where we use $10^5$ CFU/mouse. Survival is scored over a period of at least 5 days. Clearance of Bacteria: 36 h after injection of *K. pneumoniae*, mice are anesthetized by intraperitoneal injection of tribromoethanol. Blood is taken by heart puncture. For preparation of plasma, 450 µl of blood is added to 50 µl of sodium citrate (0.1 M). Immediately thereafter, mice are killed by cervical dislocation. Then, mice are perfused with 10 ml of a 0.9% NaCl solution to wash out the blood. The liver, spleen, and kidney are removed aseptically, weighed, and homogenized mechanically in sterile saline. For homogenization, the liver is diluted (w/v) 2-fold; spleen and kidney are diluted 10-fold. The suspensions are diluted and plated out on sterile nutrient agar. After overnight incubation at 37° C., CFU numbers are counted. Measurement of a 1-AGP—The concentration of a 1-AGP in mouse serum is measured using a home-developed sandwich enzyme-linked immunosorbent assay. A rat monoclonal antibody is coated (0.1 mg/ml) on 96-well Maxisorb plates. After blocking with 1% BSA and PBS, samples and a murine a 1-AGP standard are titrated, after which the plates are incubated for 1 h at 37° C. A rabbit polyclonal antiserum (1/1,000) and subsequent alkaline phosphatase-conjugated anti-rabbit antibody (1/5,000) are used as secondary and third anti-body. Human a 1-AGP is measured by nephelometry using a goat anti-human a 1-AGP polyclonal antibody. Effect of CpdA against a lethal Infection with *K. pneumoniae*: to investigate whether CpdA confers protection, mice are pre-treated with CpdA 24 or 48 h before a lethal bacterial challenge ($10^6$ CFU unless otherwise stated) of *K. pneumoniae*. CpdA is administered systemically (iv or ip) or locally (intra-articular) by injection. In case of low stability/rapid clearance of the active compound, use of peristaltic pump is beneficial for continuous flow and accumulation of the latter compound at tissue under investigation. Cpd A is administered at a dose preferably 10 times more concentrated than prednisolone, most preferably in the same dose range as described in detail by Alegre et al. (J. Immunol. 1991, vol 146, p. 1184).

11.6. Beneficial effects of Cpd A in Atopic Diseases (Asthma, Allergy)

An experimental in/ex vivo asthma model as described in detail by Hart et al. (Am J Respir Crit Care Med. January 2000; 161(1):224–31) is used in the present experiment. Briefly, it is determined whether inhaled CpdA therapy modulates the activity of the transcription factor, nuclear factor kappa B (NF-κB) during asthma. Individuals with mild asthma undergo bronchoalveolar lavage (BAL) with bronchial biopsies in a double-blind, placebo-controlled and crossover study after placebo or after inhaled CpdA (dose preferably 10 times more concentrated than for corticoids, most preferably same dose range i.e. 500 µg twice daily).

An experimental in/ex vivo (psoriasis) model as described in detail in Beyaert et al. (Eur J Immunol. August 1992; 22(8):2181–4) is also used. Briefly fifty µl of PBS containing TNF+LiCl are injected subcutaneous into the back of mice which induces a psoriasiform inflammatory reaction. Effects of Cpd A will be analysed on skin biopts. The animals are killed by cervical dislocation at different time intervals. Skin fragments with a diameter of 4 mm are removed and analysed by histo-immunochemistry or immersed in PBS and frozen at −20C. Later on, skin fragments are thawed and homogenized in PBS by 30 strokes with a Dounce homogenizer and centrifuged at 15000× g for 10 min. Supernatants are tested for functional cytokine activity by appropriate ELISA or bioassay. Cpd A will be applied by a transdermal device at a dose preferably 10 times more concentrated than prednisolone, most preferably the same (therapeutic effective) dose.

11.7. Beneficial Effects of Cpd A in Virus Replication Models

As replication of HIV-virus is NFkB dependent, Cpd A may be beneficial to downregulate HIV replication (see Kurata Si & Yamamoto NJ, Cell Biochem. 1999; 76(1):13–9 and DeLuca et al. Cytokine Growth Factor Rev. September–December 1999; 10(3–4): 235–53).

An experimental, promyelocytic model of latency as described in detail by Critchfield et al. (Antivir Chem Chemother. September 1999; 10(5):275–84) is used in the present experiment.Cpd A is administered according to Critchfield et al. (Antivir Chem Chemother. September 1999; 10(5):275–84) at a dose preferably 10 times more concentrated than prednisolone, most preferably in the same dose range (preferentially $10-5$ to $10-9$ M).

11.8. Test Beneficial Effects of Cpd A in Parasite Infection Models

As TNF-induced NFkB is an important therapeutic target during parasitic infections, Cpd A is beneficial in treating parasitic infections. An experimental murine Plasmodium chabaudi chabaudi model as described in detail in Scorza et al. (Parasite Immunol. November 1999; 21(11):545–54) is being used. CpdA is administered systemically (iv or ip) or locally (intra-articular) by injection. In case of low stability/ rapid clearance of the active compound, use of peristaltic pump is beneficial for continuous flow and accumulation of the lafter compound at tissue under investigation. Cpd A is administered at a dose preferably 10 times more concentrated than prednisolone, most preferably in the same dose range as described in detail by Alegre et al. (J. Immunol. 1991, vol 146, p. 1184).

11.9. Beneficial Effects of CpdA in Cancer

As NFkB plays a role in cancer and apoptosis, NFkB inhibitors such as CpdA are beneficial as chemotherapy sensitizers.

An experimental ex vivo model CLL as described in detail in Van Causbroeck et al. Tijdschrift van de Belgische Vereniging voor Laboratoriumtechnologen December, 2000 is being used.

Cpd A is administered as described in Van Causbroeck et al. (Tijdschrift van de Belgische Vereniging voor Laboratoriumtechnologen December, 2000) at a dose preferably 10 times more concentrated than prednisolone, most preferably at the same dose range (preferentially $10^{-5}$ to $10^{-9}$M).

REFERENCES

Auphan, N., J. A. DiDonato, et al. (1995). "Immunosuppression by glucocorticoids: inhibition of NF-kappa B activity through induction of I kappa B synthesis." Science 270(5234)): 286–90.

Baldwin, A. S., Jr. (1996). "The NF-kappa B and I kappa B proteins: new discoveries and insights." Annu Rev Immunol 14: 649–683.

Barnes, P. J. and 1. M. Adcock (1997). "NF-kappa B: a pivotal role in asthma and a new target for therapy." Trends Pharmacol Sci 18(2): 46–50.

Barnes, P. J. and 1. M. Adcock (1998). "Transcription factors and asthma." Eur Respir J 12: 221–234.

Basson, P. A., J. C. Morgenthal, et al. (1969). ""grootlamsiekte", a specific syndrome of prolonged gestation in sheep caused by a shrub, Salsola tuberculata (Fenzl ex Moq) Schinz. var. tomentosa C.A. Smith ex Aellen." Onderstepoort J. Vet. Res. 36: 59–103.

Beato, M., P. Herrlich, et al. (1995). "Steroid hormone receptors: many actors in search of a plot." Cell 83(6): 851–7.

Boone, E., V. Vandevoorde, et al. (1998). "Activation of p42/p44 mitogen-activated protein kinases (MAPK) and p38 MAPK by tumor necrosis factor (TNF) is mediated through the death domain of the 55-kDa TNF receptor." FEBS Lett 441(2)): 275–80.

Brondegaard, V. J. (1973). "Contraceptive plant drugs." Planta Med. 23: 167–172.

Brostjan, C., J. Anrather, et al. (1996). "Glucocorticoid-mediated repression of NFkappaB activity in endothelial cells does not involve induction of IkappaBalpha synthesis." J Biol Chem 271(32)): 19612–6.

Caelles, C., J. M. Gonzalez Sancho, et al. (1997). "Nuclear hormone receptor antagonism with AP-1 by inhibition of the JNK pathway." Genes Dev. 11(24): 3351–3364.

Cato, A. C. and E. Wade (1996). "Molecular mechanisms of anti-inflammatory action of glucocorticoids." Bioessays 18(5)): 371–8.

De Bosscher, K., M. L. Schmitz, et al. (1997). "Glucocorticoid-mediated repression of nuclear factor-kappaB-dependent transcription involves direct interference with transactivation." Proc Natl Acad Sci U S A 94(25)): 13504–9.

De Bosscher, K., W. Vanden Berghe, et al. (2000). "Glucocorticoids repress NF-kB-driven genes by disturbing the interaction of p65 with the basal transcription machinery, irrespective of coactivator levels in the cell." Proc. Natl. Acad. Sci. 97(8): 3919–3924.

Ghosh, S., M. J. May, et al. (1998). "NF-kappa B and rel proteins: evolutionarily conserved mediators of immune responses." Annu Rev Immunol 16: 225–260.

Graham, F. L. and A. J. Van der Eb (1973). "A new technique for the assay of infectivity of human adenovirus 5 DNA." Virology 52: 456–467.

Heck, S., K. Bender, et al. (1997). "I kappaB alpha-independent downregulation of NF-kappaB activity by glucocorticoid receptor." EMBO J 16(15)):4698–707.

Karin, M. (1996). "The regulation of AP-1 activity by mitogen-activated protein kinases." Philos Trans R Soc Lond B Biol Sci 351(1336): 127–134.

Karin, M., Z. G. Liu, et al. (1997). "AP-1 function and regulation." Curr Opin Cell Biol 9(2): 240–246.

Louw, A. and P. Swart (1999). "Salsola tuberculatiformis Botsch. and an Aziridine Precursor Analog Mediate the in vivo Increase in Free Corticosterone and Decrease in Corticoisteroid-binding Globulin in Female Wistar Rats." Endocrinology 140(5): 2044–2053.

Louw, A., P. Swart, et al. (2000). "Influence of an aziridine precursor on the in vitro binding parameters of rat and ovine corticosteroid-binding globulin (CBG)." Biochem. Pharmacol. 59(2): 167–175.

Louw, A., P. Swart, et al. (1997). "Mechanism for the Stabilization in vivo of the Aziridine Precursor 2-(4-acetoxyphenyl)-2-chloro-N-methyl-ethylammonium Chloride by Serum Proteins." Biochemical Pharmacology 53: 189–197.

May, M. J. and S. Ghosh (1997). "Rel/NF-kappa B and I kappa B proteins: an overview." Semin Cancer Biol 8(2): 63–73.

May, M. J. and S. Ghosh (1998). "Signal transduction through NF-kappa B." Immunol Today 19(2): 80–88.

McEwan, I. J., A. P. Wright, et al. (1997). "Mechanism of gene expression by the glucocorticoid receptor: role of protein-protein interactions." Bioessays 19(2): 153–160.

Plaisance, S., W. Vanden Berghe, et al. (1997). "Recombination signal sequence binding protein Jkappa is constitutively bound to the NF-kappaB site of the interleukin-6 promoter and acts as a negative regulatory factor." Mol Cell Biol 17(7): 3733–3743.

Ruegg, U. and G. Burgess (1989). "Staurosporine, K-252 and UCN-01: potent but nonspecific inhibitors of protein kinases." Trends Pharmacol.Sci. 10: 218–220.

Scheinman, R.,. P. C. Cogswell, et al. (1995). "Role of transcriptional activation of i kappa b alpha in mediation of immunosuppression by glucocorticoids [see comments]." Science 270(5234): 283–286.

Scheinman, R. I., A. Gualberto, et al. (1995). "Characterization of mechanisms involved in transrepression of NF-kappa B by activated glucocorticoid receptors." Mol Cell Biol 15(2)): 943–53.

Tamaoki, T., H. Nomotok, et al. (1986). "Staurosporine, a potent inhibitor of phospholipid/Ca-dependent protein kinase." Biochem Biophys Res Commun 135: 397–402.

Van de Stolpe, A., E. Caldenhoven, et al. (1993). "Glucocorticoid-mediated repression of intercellular adhesion molecule-1 expression in human monocytic and bronchial epithelial cell lines." Am J Respir Cell Mol Biol 8(3): 340–347.

van der Burg, B., J. Liden, et al. (1997). "Nuclear Factor-Kappa B Repression in Antiinflammation and Immunosuppression by Glucocorticoids." TEM 8(4): 152–157.

van der Merwe, K. J., J. H. S. Hofmeyr, et al. (1976). "Natural products affecting the gestation period of sheep and their mode of action." S Afr J Sci 72: 184.

Vanden Berghe, W., E. Francesconi, et al. (1999). "Dissociated Glucocorticoids with Antiinflammatory Potential Repress Interleukin-6 Gene Expression by an NF-kappa-B-Dependent Mechanism." Mol Pharmacol 56: 797–806.

Vanden Berghe, W., S. Plaisance, et al. (1998). "p38 and extracellular signal-regulated kinase mitogen-activated protein kinase pathways are required for nuclear factor-kappaB p65 transactivation mediated by tumor necrosis factor." J Biol Chem 273(6): 3285–3290.

Vanhoenacker, P., W. Fiers, et al. (1994). "Studies on the induction of the interleukin-6 promoter in cell lines of human and simian origin." Eur Cytokine Netw 5(3): 283–291.

Vayssière, B. M., S. Dupont, et al. (1997). "Synthetic glucocorticoids that dissociate transactivation and AP-1 transrepression exhibit antiinflammatory activity in vivo." Mol Endocrinol 11(9): 1245–1255.

What is claimed is:

1. A method of treating a mammalian subject having an inflammatory disease or inflammation-associated disorder comprising administering a therapeutically effective amount of a compound of formula (I)

(I)

or its aziridine derivative, wherein R is an acyloxy group, X is a hydrogen, or halogen, and Y is a lower alkyl group of one to four carbons, to the mammalian subject in the absence of concomitant administration of a corticosteroid.

2. The method according to claim 1, wherein administering a therapeutically effective amount of a compound of formula (I) comprises administering a therapeutically effective amount of the compound of formula (I) wherein R is an acetoxy group, X is chloride, and Y is methyl.

3. The method according to claim 1, wherein said therapeutically effective amount is sufficient to inhibit expression of an IL-6 promoter.

4. The method according to claim 2, wherein said therapeutically effective amount is sufficient to inhibit expression of a pro-inflammatory gene.

5. The method according to claim 2, wherein said therapeutically effective amount is sufficient to inhibit expression of a NF-κB-dependent gene, with little or no activation of a glucocorticoid responsive element-dependent gene.

6. A method of treating a symptom of inflammation in a mammalian subject comprising administering a therapeutically effective amount of a compound of formula (I)

(I)

or its aziridine derivative, wherein R is an acetoxy group, X is chloride, and Y is methyl, to the mammalian subject in the absence of concomitant administration of a corticosteroid, thereby treating a symptom of inflammation.

7. A method of treating a mammalian subject having an inflammatory disease or inflammation-associated disorder comprising:

administering a therapeutically effective amount of a compound having anti-inflammatory activity which can be determined by measuring a decrease in transcriptional stimulation produced by the combination of the compound and TNF, relative to TNF alone, using an IL-6 promoter-driven reporter construct in L929sA cells, and determining inactivity of the compound on a GRE promoter-driven construct in L929sA cells, said compound comprising formula (I):

(I)

or its aziridine derivative, wherein R is an acyloxy group, X is a hydrogen, or halogen, and Y is a lower alkyl group of one to four carbons, to the mammalian subject in the absence of concomitant administration of a corticosteroid.

* * * * *

SEQUENCE LISTING

```
<160> NUMBER OF SEQ ID NOS: 3

<210> SEQ ID NO 1
<211> LENGTH: 66
<212> TYPE: DNA
<213> ORGANISM: Artificial Sequence
<220> FEATURE:
<223> OTHER INFORMATION: Annealed oligonucleotide

<400> SEQUENCE: 1
agatctctct gctgtacagg atgttctagc ggatcctgct gtacaggatg ttctagctac    60
ctgcag                                                              66

<210> SEQ ID NO 2
<211> LENGTH: 66
<212> TYPE: DNA
<213> ORGANISM: Artificial Sequence
<220> FEATURE:
<223> OTHER INFORMATION: Annealed oligonucleotide

<400> SEQUENCE: 2
tctagagaga cgacatgtcc tacaagatcg cctaggacga catgtcctac aagatcgatg    60
gacgtc                                                              66

<210> SEQ ID NO 3
<211> LENGTH: 25
<212> TYPE: DNA
<213> ORGANISM: Artificial Sequence
<220> FEATURE:
<223> OTHER INFORMATION: Part of oligonucleotide containing the
      NF-kappaB site

<400> SEQUENCE: 3
agctatgtgg gattttccca tgagc                                         25
```